(12) United States Patent
Ho et al.

(10) Patent No.: US 11,730,779 B2
(45) Date of Patent: Aug. 22, 2023

(54) LACTIC ACID BACTERIAL COMPOSITION FOR TREATING OR PREVENTING JAUNDICE

(71) Applicant: GLAC BIOTECH CO., LTD, Tainan (TW)

(72) Inventors: Hsieh-Hsun Ho, Tainan (TW); Yi-Wei Kuo, Tainan (TW); Jia-Hung Lin, Tainan (TW); Hui-Shan Wang, Tainan (TW); Yen-Yu Huang, Tainan (TW); Wen-Yang Lin, Tainan (TW); Ko-Chiang Hsia, Tainan (TW)

(73) Assignee: GLAC BIOTECH CO., LTD, Tainan (TW)

( * ) Notice: Subject to any disclaimer, the term of this patent is extended or adjusted under 35 U.S.C. 154(b) by 0 days.

(21) Appl. No.: 17/669,752

(22) Filed: Feb. 11, 2022

(65) Prior Publication Data
US 2023/0149480 A1 May 18, 2023

(30) Foreign Application Priority Data
Nov. 16, 2021 (TW) ................. 110142663

(51) Int. Cl.
| | |
|---|---|
| *A61K 35/747* | (2015.01) |
| *A61P 3/00* | (2006.01) |
| *A61K 35/745* | (2015.01) |
| *A61N 5/06* | (2006.01) |
| *A61K 35/00* | (2006.01) |
| *A61P 31/04* | (2006.01) |

(52) U.S. Cl.
CPC .......... *A61K 35/747* (2013.01); *A61K 35/745* (2013.01); *A61N 5/0621* (2013.01); *A61P 3/00* (2018.01); *A61P 31/04* (2018.01); *A61K 2035/115* (2013.01)

(58) Field of Classification Search
CPC ................ A61K 35/747; A61K 35/745; A61K 2035/115; A61N 5/0621; A61P 3/00
See application file for complete search history.

(56) References Cited

PUBLICATIONS

Tsai et al., US National Library of Medicine, ClinicalTrials.gov, Clinical trial study No. NCT03876678, publicly available Mar. 13, 2019 (Year: 2019).*

Chen et al. Probiotics Supplementation Therapy for Pathological Neonatal Jaundice: A Systematic Review and Meta-Analysis, 2017, Front. Pharmacol. 8:432. doi: 10.3389/fphar.2017.00432 (Year: 2017).*

* cited by examiner

*Primary Examiner* — Louise W Humphrey
*Assistant Examiner* — Alexander M Duryee
(74) *Attorney, Agent, or Firm* — Locke Lord LLP; Tim Tingkang Xia, Esq.

(57) ABSTRACT

The present invention provides a lactic acid bacterial composition for inhibiting the activity of *Escherichia coli* and/or treating or preventing jaundice, the composition including: a *Bifidobacterium animalis* subsp. *lactis* CP-9 strain and a *Lactobacillus salivarius* subsp. *salicinius* AP-32 strain. The present invention further provides a method for inhibiting growth of *Escherichia coli*, the method including the step(s) of: administering the foregoing lactic acid bacterial composition to a subject in need thereof. The present invention additionally provides a method for treating or preventing jaundice, the method including the step(s) of: administering the foregoing lactic acid bacterial composition to a subject in need thereof.

6 Claims, 4 Drawing Sheets

LACTIC ACID BACTERIAL COMPOSITION FOR TREATING OR PREVENTING JAUNDICE

CROSS REFERENCE

This non-provisional application claims priority of Taiwan Invention Patent Application No. 110142663, filed on Nov. 16, 2021, the contents thereof are incorporated by reference herein.

FIELD OF THE INVENTION

The present invention is directed to a lactic acid bacterial composition, and more particularly to a lactic acid bacterial composition for treating or preventing jaundice.

BACKGROUND OF THE INVENTION

Bilirubin is the metabolite of hemoglobin. While either hemoglobin metabolism or bilirubin excretion is abnormal, jaundice may occur. The occurrence cause of jaundice can be determined according to the contents of different types of bilirubin in the body. It is related to the abnormality of hemoglobin metabolism that the content of unconjugated bilirubin (also called "indirect bilirubin") is high, e.g., hemolysis caused by infection or drug, overproduction of blood cells, congenital and hereditary disease, or hemolytic disease; it is related to the abnormality of bilirubin excretion that the content of conjugated bilirubin (also called "direct bilirubin") is high, e.g., hepatitis caused by virus infection (hepatitis B or hepatitis C) or biliary disease (biliary obstruction, stone, tumor, cholangitis, or primary biliary cirrhosis).

Neonatal jaundice is a disease which commonly affects infants. The incidence rate of neonatal jaundice is approximately 60% to 70% in the Western countries, and even higher in the Asian countries. The common types of neonatal jaundice are physiologic jaundice and breastfeeding jaundice. Generally, while the infant's liver is immature, the ability to absorb, convert, and excrete bilirubin is so poor that bilirubin is left over in blood and physiologic jaundice occurs. Physiologic jaundice usually occurs on the 2nd day to 7th day after birth, and the symptom is the most serious in the 1st week after the symptom occurs and then is gradually lost. In other words, while the infant's liver is immature, unconjugated bilirubin can't be metabolized to make its content elevated in the body. The high concentration of unconjugated bilirubin flows back to blood through the liver and the intestine so that the icteric index is high enough to lead to physiologic jaundice. The therapy against physiologic jaundice is phototherapy, in which unconjugated bilirubin is converted into non-toxic isomers with blue light (wavelength: 425 nm to 457 nm) to excrete from the body. Breastfeeding jaundice usually occurs on the 4th day to 14th day after birth. While specific ingredients in the breast milk (e.g., progesterone or fatty acid) interfere in the conjugation of protein and bilirubin, the bilirubin conversion retards to lead to breastfeeding jaundice. Other types of neonatal jaundice are pathological jaundice, obstructive jaundice, and kernicterus, and their occurrence causes are so complicated that it is determined whether surgical operation or other therapy is performed or not after doctor's diagnosis.

In current research, the intestinal microflora in infants with jaundice and infants without jaundice is analyzed to compare the difference of intestinal microflora. By such a way, jaundice may be eliminated by changing the balance of intestinal microflora. In China Invention Patent Application No. CN106038609A, next generation sequencing (NGS) is introduced to identify the intestinal bacterial strains in infants with jaundice and those in infants without jaundice, and it is found that *Bifidobacterium* and *Bacteroides* in the infant's intestine with jaundice is less than those in the infant's intestine without jaundice. In China Invention Patent Publication No. CN101450083B, taking *Clostridium butyricum* viable bacteria can eliminate feeding intolerance in newborn infants comprising decreasing the lasting hours of jaundice, but the change of irradiation hours and icteric index is not analyzed. Nowadays, the adjuvant therapy against jaundice by taking probiotics can't bring obvious effect on decrease of the icteric index or the irradiation hours.

Therefore, there is a need to develop a bacterial strain used for the adjuvant therapy against jaundice so as to efficiently decrease the icteric index or the irradiation hours.

SUMMARY OF THE INVENTION

It is well known that lactic acid bacteria are safe and widely-used probiotics. The common lactic acid bacteria belong to *Lactobacillus, Lactococcus, Pediococcus, Enterococcus, Streptococcus, Bifidobacterium, Bacillus*, or *Leuconostoc*.

An objective of the present invention is to develop a lactic acid bacterial composition, which can inhibit the activity of enteropathogenic *Escherichia coli* to decrease the production of β-glucuronidase. As described in J Hepatol. 2005 February; 42(2):170-2, pathogenic bacteria can produce a lot of β-glucuronidase in the gastrointestinal tract to affect the bilirubin metabolism in the body. Since the mentioned lactic acid bacterial composition has the ability to inhibit the activity of enteropathogenic *Escherichia coli* so as to decrease the production of β-glucuronidase, it can be clinically used for decrease of the icteric index to treat or prevent jaundice.

Accordingly, the present invention provides a lactic acid bacterial composition for inhibiting the activity of *Escherichia coli* and/or treating or preventing jaundice, the composition including: a *Bifidobacterium animalis* subsp. *lactis* CP-9 strain (accession number: CCTCC M2014588) or a *Lactobacillus salivarius* subsp. *salicinius* AP-32 strain (accession number: CCTCC M2011127).

Since the *Bifidobacterium animalis* subsp. *lactis* CP-9 strain and the *Lactobacillus salivarius* subsp. *salicinius* AP-32 strain can inhibit the growth of *Escherichia coli*, the composition in accordance with the present invention has potential to be used for the inhibition of the activity of *Escherichia coli* and/or the treatment or prevention of jaundice.

The present invention further provides a method for inhibiting growth of *Escherichia coli*, the method including the step(s) of: administering the foregoing lactic acid bacterial composition to a subject in need thereof.

The present invention additionally provides a method for treating or preventing jaundice, the method including the step(s) of: administering the foregoing lactic acid bacterial composition to a subject in need thereof.

DETAILED DESCRIPTION OF THE INVENTION

Figure 1B:
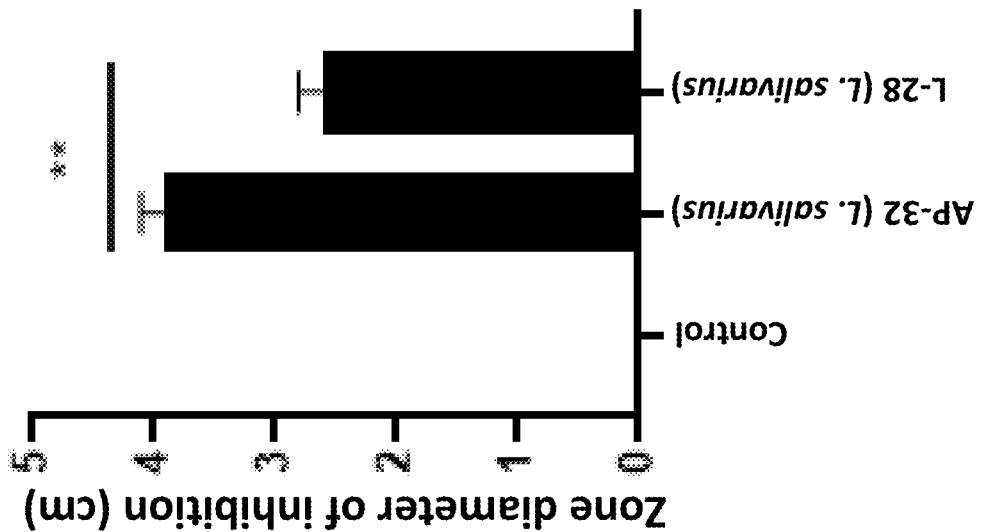
FIG. 1B is a bar graph illustrating the effect of different *Lactobacillus salivarius* subsp. *salicinius* stains on the growth of *Escherichia coli;*

The detailed description and preferred embodiments of the invention will be set forth in the following content, and provided for people skilled in the art to understand the characteristics of the invention.

Each lactic acid bacterial strain according to the present invention is deposited at the Food Industry Research and Development Institute in No. 331 Shih-Pin Road, Hsinchu, Taiwan and at the China Center for Type Culture Collection in Wuhan University, Wuhan City, China in the form of freeze-dried culture. The deposition information is listed in Table 1 below.

TABLE 1

Deposition Information

| Strain | Classification | Related Patent | Accession Number | Deposition Date |
|---|---|---|---|---|
| CP-9 | *Bifidobacterium animalis* subsp. *lactis* | Taiwan Invention Patent No. 1572713 | BCRC 910645 | Aug. 21, 2014 |
| | | China Invention Patent No. CN105985918B | CCTCC M2014588 | Nov. 24, 2014 |
| AP-32 | *Lactobacillus salivarius* subsp. *salicinius* | Taiwan Invention Patent No. 1384990 | BCRC 910437 | Jul. 30, 2009 |
| | | China Invention Patent No. CN102835666B | CCTCC M2011127 | Apr. 10, 2011 |

It is found in the present invention that a *Bifidobacterium animalis* subsp. *lactis* CP-9 strain and a *Lactobacillus salivarius* subsp. *salicinius* AP-32 strain can inhibit the growth of enteropathogenic *Escherichia coli*, which can produce β-glucuronidase, so that the icteric index and the irradiation hours both can decrease. Especially, the combination of these bacterial strains can bring a synergistic effect on the inhibition of the *Escherichia coli* growth. Therefore, these bacterial strains can be used for inhibiting the activity of *Escherichia coli* and/or treating or preventing jaundice, alone or together.

An embodiment of the present invention discloses a lactic acid bacterial composition. The composition can inhibit the activity of *Escherichia coli* and/or treat or prevent jaundice, and comprises: a *Bifidobacterium animalis* subsp. *lactis* CP-9 strain or a *Lactobacillus salivarius* subsp. *salicinius* AP-32 strain. Preferably, the composition comprises: the *Bifidobacterium animalis* subsp. *lactis* CP-9 strain and the *Lactobacillus salivarius* subsp. *salicinius* AP-32 strain.

Preferably, the composition is a food composition or a pharmaceutical composition. Preferably, the composition additionally comprises: a physiologically acceptable excipient, diluent, or carrier.

On the condition that the composition is a food composition, the physiologically acceptable excipient, diluent, or carrier is an edible acceptable excipient, diluent, or carrier, and an example thereof is a food, but not limited thereto. The food may be a fluid milk product (e.g., a milk or an evaporated milk), a fermented milk product (e.g., a fermented milk), a milk powder, an ice cream, a cheese, a soy milk, a fermented soy milk, a vegetable juice, a fruit juice, a sports drink, a jelly, a cookie, an energy bar, a healthy food, an animal feed, or a dietary supplement, but not limited thereto.

On the condition that the composition is a pharmaceutical composition, the physiologically acceptable excipient, diluent, or carrier is a pharmaceutically acceptable excipient, diluent, or carrier and an example thereof is a solution, a buffer, an emulsifier, a suspension agent, a decomposing agent, a disintegrant, a dispersant, a binder, a stabilizer, a chelation agent, a gelling agent, a humectant, a lubricant, an absorption delaying agent, and a liposome, but not limited thereto. The composition may be in the oral dosage form or the parenteral dosage form. An example of the oral dosage form is a powder, a lozenge, a tablet, a troche, a pill, a capsule, a solution, a suspension, an emulsion, a syrup, an elixir, a thick paste, or a drop, but not limited thereto; an example of the parenteral dosage form is a liquid, but not limited thereto. The term "parenteral dosage form" used in the present content comprises: a subcutaneous dosage form, an intramuscular dosage form, an intravertebral dosage form, an intravenous dosage form, or a sublingual dosage form, but not limited thereto.

The *Bifidobacterium animalis* subsp. *lactis* CP-9 strain and the *Lactobacillus salivarius* subsp. *salicinius* AP-32 strain may be separately be a viable bacterial strain or a deactivated bacterial strain. On the condition that the composition comprises: the *Bifidobacterium animalis* subsp. *lactis* CP-9 strain and the *Lactobacillus salivarius* subsp. *salicinius* AP-32 strain, the number ratio of the CP-9 strain and the AP-32 strain may be 1:9 to 9:1, preferably 1:1 to 9:1.

Another embodiment of the present invention discloses a method for inhibiting growth of *Escherichia coli* and a method for treating or preventing jaundice. Each method comprises: administering the foregoing lactic acid bacterial composition to a subject in need thereof.

The foregoing composition can be administered to the subject in need of inhibiting growth of *Escherichia coli* to achieve the purpose of inhibition of the *Escherichia coli* growth. The term "subject" used in the present content comprises: a mammal, but not limited thereto; an example thereof is a human, a monkey, a cow, a sheep, a horse, a swine, a goat, a dog, a cat, a mouse, or a rat, but not limited thereto. The phrase "inhibiting growth of *Escherichia coli*" used in the present content comprises: reducing, alleviating, or terminating the growth or spread of *Escherichia coli*, or preventing the growth or spread of *Escherichia coli*. Based on the composition's property to inhibit growth of *Escherichia coli*, the composition can be administered to a subject in need of treating or preventing a disease caused by *Escherichia coli*, e.g., urinary tract infection or gastrointestinal infection.

The foregoing composition can be administered to the subject in need of treating or preventing jaundice to achieve the purpose of jaundice treatment or prevention. Additionally, phototherapy can be performed on the subject before, during, and/or after the composition administration. What's more, the foregoing composition can be administered to the subject in need of treating or preventing jaundice to decrease the icteric index so as to achieve the purpose of jaundice treatment or prevention. Furthermore, the foregoing composition can be administered to the subject in need of treating or preventing jaundice to decrease the irradiation hours. The term "subject" used in the present content comprises: a mammal, but not limited thereto; an example thereof is a human, a monkey, a cow, a sheep, a horse, a swine, a goat, a dog, a cat, a mouse, or a rat, but not limited thereto. The term "jaundice" used in the present content comprises: jaundice resulted from high content of conjugated bilirubin caused by adult liver disease or biliary disease, e.g., jaundice caused by virus hepatitis (hepatitis B or hepatitis C) or jaundice caused by biliary disease (e.g., biliary obstruction, stone, tumor, cholangitis, or primary biliary cirrhosis), but not limited thereto. The term "jaundice" used in the present content comprises: jaundice caused by infant's immature liver or jaundice derived from urinary tract infection caused by *Escherichia coli*, but not limited thereto.

The following examples are offered to further illustrate the present invention:

Example 1

Manufacture of Bacterial Powders

All bacterial strains were cultivated in an MRS medium containing 0.05% cysteine at 37° C. for 24 hours to activate these strains. $1\times10^8$ CFU activated bacterial strains were seeded into a 5 mL MRS medium containing 60 mg/mL glucose and 0.05% cysteine at a volume concentration of 2%, and cultivated at 37° C. for 20 hours. Afterwards, the thus-obtained culture was centrifugated at a rate of 3,000 rpm for 10 minutes, and the supernatant was removed and the precipitate was washed with 0.1M PBS. After which, the strain concentration of the bacterial solution was adjusted to $1\times10^{10}$ CFU/mL with PBS, and the bacterial solution was lyophilized to obtain bacterial powders for the following experiment.

Example 2

Analysis for *Escherichia coli* Growth

Lactic acid bacterial strains (total bacterial concentration of $1\times10^9$ CFU/mL) were coated on a solid medium to form a width of 2 cm; a blank solid medium was used as the control group. After cultivation for 2 days, a 14 mL medium for pathogenic bacteria was injected and solidified. Afterwards, the pathogenic bacterial solution containing *Escherichia coli* was uniformly coated on the solidified medium. After cultivation for a proper period, the zone diameter of inhibition on the bacterial plate was measured with a ruler to analyze the inhibitory activity by lactic acid bacterial strains.

Figure 1A:
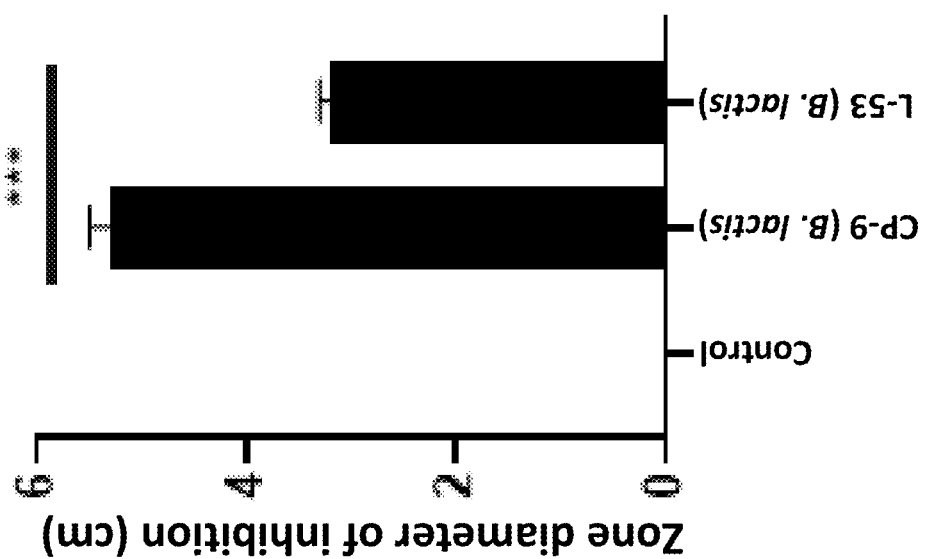
FIG. 1A is a bar graph illustrating the effect of different *Bifidobacterium animalis* subsp. *lactis* stains on the growth of *Escherichia coli*.

As shown in FIG. 1A, with the same total bacterial number, the zone diameter of *Escherichia coli* inhibition by CP-9 strains was 5.3±0.2 cm; the zone diameter of *Escherichia coli* inhibition by L-53 strains was 3.2±0.1 cm. The foregoing result implies that although CP-9 strains and L-53 strains all belong to *Bifidobacterium animalis* subsp. *lactis*, the inhibitory activity for *Escherichia coli* by CP-9 strains is greater than that by L-53 strains.

As shown in FIG. 1B, with the same total bacterial number, the zone diameter of *Escherichia coli* inhibition by AP-32 strains was 3.9±0.2 cm; the zone diameter of *Escherichia coli* inhibition by L-28 strains was 2.6±0.2 cm. The foregoing result implies that although AP-32 strains and L-28 strains all belong to *Lactobacillus salivarius* subsp. *salicinius*, the inhibitory activity for *Escherichia coli* by AP-32 strains is greater than that by L-28 strains.

According to the conclusion made from FIGS. 1A to 1B, different bacterial strains belonging to the same species have various inhibitory activities for *Escherichia coli*.

Figure 1D:
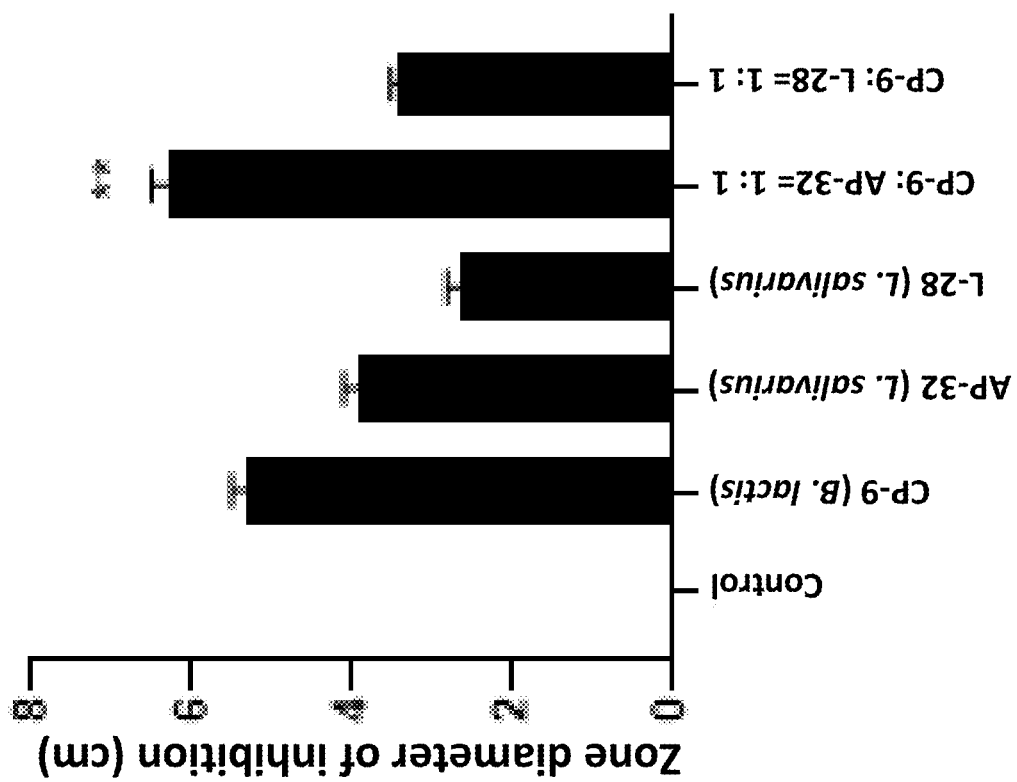
FIG. 1D is a bar graph illustrating the effect of various bacterial compositions on the growth of *Escherichia coli;*
Figure 1C:
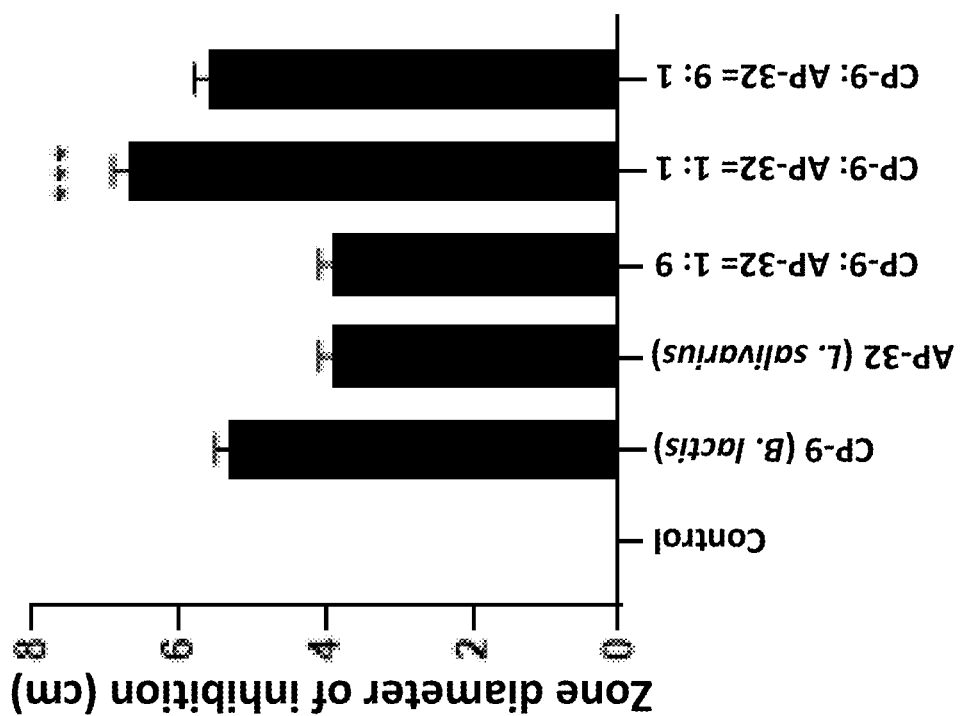
FIG. 1C is a bar graph illustrating the effect of different mixing ratios of *Bifidobacterium animalis* subsp. *lactis* CP-9 strains and *Lactobacillus salivarius* subsp. *salicinius* AP-32 strains on the growth of *Escherichia coli;*

As shown in FIG. 1C, with the same total bacterial number, the zone diameter of *Escherichia coli* inhibition by CP-9 strains and AP-32 strains at a number ratio of 1:9 was 3.9±0.2 cm; the zone diameter of *Escherichia coli* inhibition by CP-9 strains and AP-32 strains at a number ratio of 1:1 was 6.7±0.2 cm; the zone diameter of *Escherichia coli* inhibition by CP-9 strains and AP-32 strains at a number ratio of 9:1 was 5.9±0.2 cm. Since the zone diameter of *Escherichia coli* inhibition by CP-9 strains and AP-32 strains at a number ratio of 1:1 and the zone diameter of *Escherichia coli* inhibition by CP-9 strains and AP-32 strains at a number ratio of 9:1 were greater than the zone diameter of *Escherichia coli* inhibition only by CP-9 strains and the zone diameter of *Escherichia coli* inhibition only by AP-32 strains, this result implies that on the condition that CP-9 strains and AP-32 strains are at a number ratio of 1:1 to 9:1, the combination of these kinds of strains has a synergistic activity on the inhibition of the *Escherichia coli* growth.

As shown in FIG. 1D, with the same total bacterial number, the zone diameter of *Escherichia coli* inhibition by CP-9 strains and AP-32 strains at a number ratio of 1:1 was 6.3±0.2 cm; the zone diameter of *Escherichia coli* inhibition by CP-9 strains and L-28 strains at a number ratio of 1:1 was 3.4±0.1 cm. Since the zone diameter of *Escherichia coli* inhibition by CP-9 strains and AP-32 strains at a number ratio of 1:1 was greater than the zone diameter of *Escherichia coli* inhibition only by CP-9 strains and the zone diameter of *Escherichia coli* inhibition only by AP-32 strains, and the zone diameter of *Escherichia coli* inhibition by CP-9 strains and L-28 strains at a number ratio of 1:1 was greater than the zone diameter of *Escherichia coli* inhibition only by L-28 strains but smaller than the zone diameter of *Escherichia coli* inhibition only by CP-9 strains, this result implies that although AP-32 strains and L-28 strains all belong to *Lactobacillus salivarius* subsp. *salicinius*, only the combination of CP-9 strains and AP-32 strains brings a synergistic effect on the inhibition of the *Escherichia coli* growth.

Example 3

Analysis for Irradiation Hours and Icteric Index 137 infants were preliminarily chosen from the Pediatric Newborn Observation Room in the China Medical University Children's Hospital. All infants were full-term infants (≥37 weeks) and had the icteric index on the 4th day after birth of greater than 15 mg/dL. However, 16 infants were excluded based on that each had one of the following diseases: (1) hypothyroidism; (2) Down syndrome; (3) ABO hemolytic disease; (4) gastrointestinal disease; (5) G6PD deficiency (favism); (6) hemangioma; (7) cephalematoma; (8) severe perinatal asphyxia; (9) neonatal chromosome disorder; (10) cyanotic congenital heart disease; (11) omphalocele; (12) early onset sepsis; and (13) liver failure, and finally the other 121 infants were used as testers.

Subsequently, the 121 testers were randomly divided in three groups: (1) a group with CP-9 strain administration and phototherapy; (2) a group with AP-32 strain administration and phototherapy; and (3) a group with placebo administration and phototherapy. All testers received phototherapy, in which the light for irradiation was blue light with a wavelength of 425 nm to 457 nm, and the irradiation hours were determined according to the gestational age, the infant's age and the symptoms of the complication. The phototherapy standard is listed in Table 2 below.

TABLE 2

Phototherapy Standard Against Jaundice

| | Condition | | | |
|---|---|---|---|---|
| | Gestational age of 35 weeks to 37 weeks and 6 days; Gestational age ≥38 weeks but having the risk to suffer from other complications | | Gestational age ≥38 weeks | |
| Infant's age | Normal irradiance | Intensive irradiance | Normal irradiance | Intensive irradiance |
| 12 hours | 6 | 7.5 | 7.5 | 9 |
| 24 hours | 8 | 10 | 10 | 11.5 |
| 36 hours | 9.5 | 11.5 | 11.5 | 13.5 |
| 48 hours | 12 | 13 | 13 | 15 |
| 60 hours | 12.5 | 14.5 | 14.5 | 16.5 |
| 72 hours | 13.5 | 15.5 | 15.5 | 17.5 |
| 3.5 days | 14 | 16.5 | 16.5 | 19 |
| 4 days | 14.5 | 17 | 17 | 20 |
| 4.5 days | 15 | 18 | 18 | 20.5 |
| ≥5 days | 15 | 18 | 18 | 21 |

The group with CP-9 strain administration and phototherapy and the group with AP-32 strain administration and phototherapy were fed with $5 \times 10^9$ CFU bacterial strains every morning and every afternoon during the phototherapy course; the group with placebo administration and phototherapy were fed with maltodextrin at the same content as the foregoing bacterial strains every morning and every afternoon during the phototherapy course. Before feeding, the corresponding powders were mixed with breast milk or infant formula for feeding. Additionally, the blood samples were taken from the admission day to the discharge day, and the bilirubin concentrations were analyzed.

Firstly, serum bilirubin concentrations of all testers on the admission day were not significantly different, and serum bilirubin concentrations of all testers on the discharge day were also not significantly different. Next, the descent rate of each tester's icteric index was measured with the following formula:

$$\text{Descent rate (mg/dL/hr)} = \frac{\text{Decrement of icteric index}}{\text{Irradiation hours}}.$$

Figure 2:
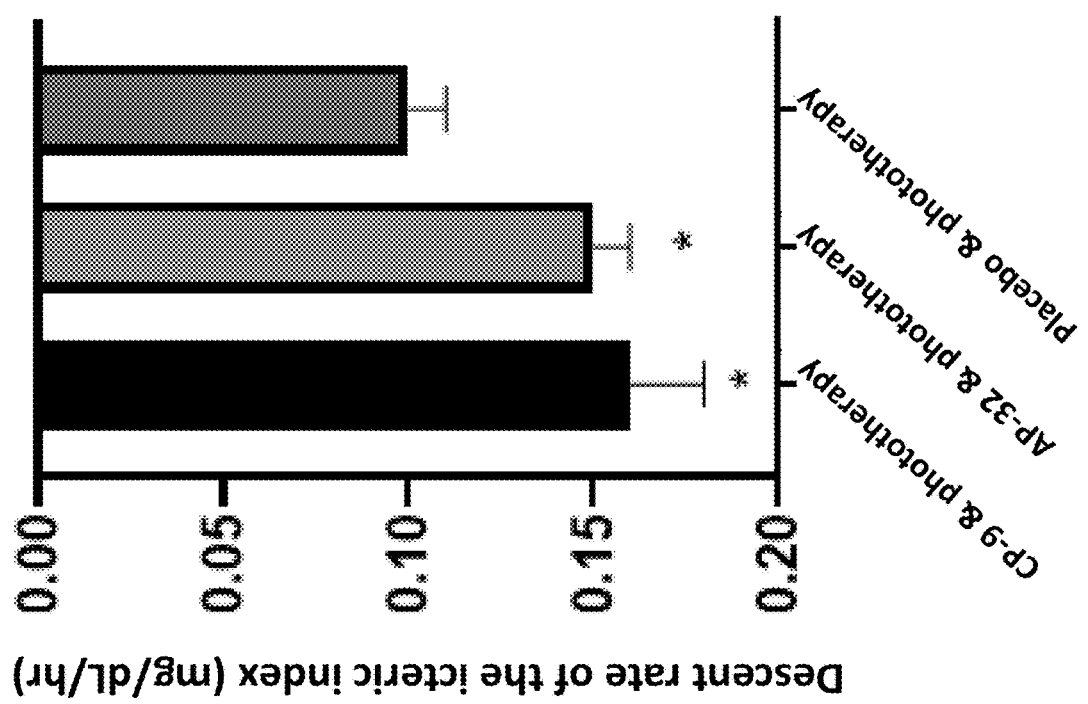
FIG. 2 is a bar graph illustrating the effect of administration of different lactic acid bacterial strains in conjugation with phototherapy on the icteric indices.

As shown in FIG. 2, the descent rate of the icteric index of the group with CP-9 strain administration and phototherapy was 0.16±0.02 mg/dL/hr, and the descent rate of the icteric index of the group with AP-32 strain administration and phototherapy was 0.155±0.017 mg/dL/hr. Both were greater than the descent rate of the icteric index of the group with placebo administration and phototherapy, 0.1±0.01 mg/dL/hr. This result implies that CP-9 strains and AP-32 strains can reduce the icteric index.

Figure 3:
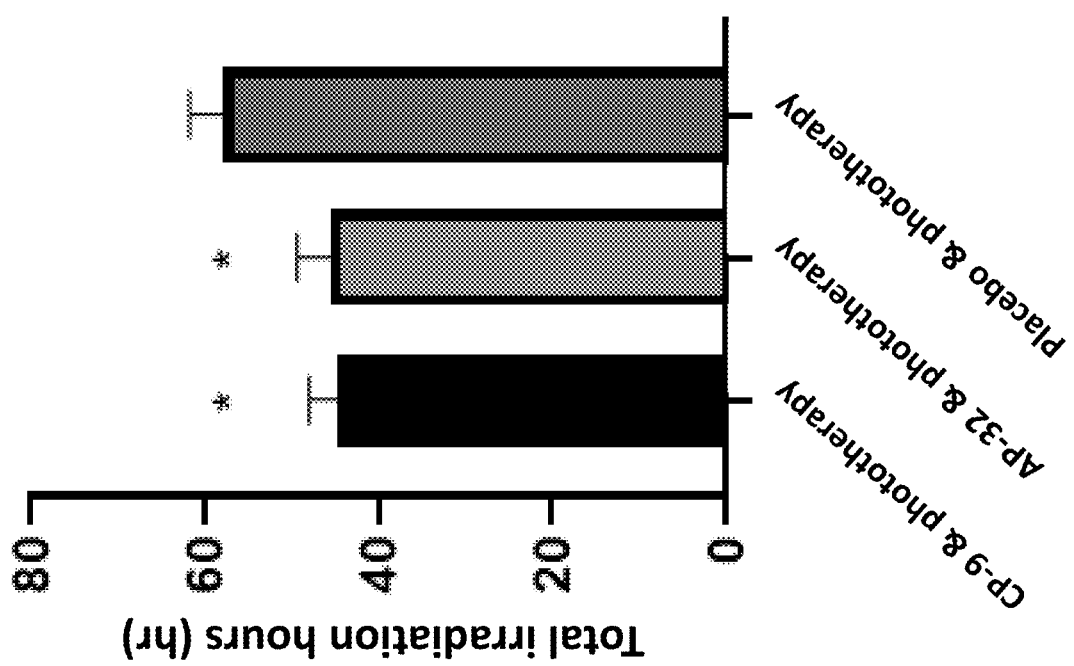
FIG. 3 is a bar graph illustrating the effect of administration of different lactic acid bacterial strains in conjugation with phototherapy on the total irradiation hours.

As shown in FIG. 3, the total irradiation hours of the group with CP-9 strain administration and phototherapy were 44.82±3.23 hr, and the total irradiation hours of the group with AP-32 strain administration and phototherapy were 45.49±3.91 hr. Both were lower than total irradiation hours of the group with placebo administration and phototherapy, 57.80±4.02 hr. This result implies that CP-9 strains and AP-32 strains can reduce the total irradiation hours.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for treating jaundice, comprising:
   administering a lactic acid bacterial composition to a subject in need thereof; and
   performing phototherapy on the subject;
   wherein the lactic acid bacterial composition comprises: a *Bifidobacterium animalis* subsp. *lactis* CP-9 strain and a *Lactobacillus salivarius* subsp. *salicinius* AP-32 strain;
   wherein the CP-9 strain is deposited at the China Center for Type Culture Collection with accession number: CCTCC M2014588 and the AP-32 strain is deposited at the China Center for Type Culture Collection with accession number: CCTCC M2011127;
   wherein a CFU ratio of the CP-9 strain and the AP-32 strain is 1:1 to 9:1;
   wherein the jaundice is jaundice derived from urinary tract infection caused by *Escherichia coli*.

2. The method as claimed in claim 1, wherein, a CFU ratio of the CP-9 strain and the AP-32 strain is 1:1.

3. The method as claimed in claim 1, wherein
   the phototherapy is performed on the subject before, during, and/or after the composition administering step.

4. The method as claimed in claim 1, wherein a CFU ratio of the CP-9 strain and the AP-32 strain is 9:1.

5. The method as claimed in claim 2, wherein the phototherapy is performed on the subject before, during, and/or after the composition administering step.

6. The method as claimed in claim 4, wherein the phototherapy is performed on the subject before, during, and/or after the composition administering step.

\* \* \* \* \*